(12) United States Patent
Albertelli et al.

(10) Patent No.: US 12,708,690 B2
(45) Date of Patent: Aug. 18, 2026

(54) ANTI-MICROBIAL FILTER

(71) Applicant: Acell Industries Limited, Dublin (IE)

(72) Inventors: Aldino Albertelli, Dublin (IE); Roberto Zedda, Dublin (IE)

(73) Assignee: ACELL INDUSTRIES LIMITED, Dublin (IE)

( * ) Notice: Subject to any disclaimer, the term of this patent is extended or adjusted under 35 U.S.C. 154(b) by 617 days.

(21) Appl. No.: 17/926,852

(22) PCT Filed: May 20, 2021

(86) PCT No.: PCT/EP2021/063466
§ 371 (c)(1),
(2) Date: Nov. 21, 2022

(87) PCT Pub. No.: WO2021/234086
PCT Pub. Date: Nov. 25, 2021

(65) Prior Publication Data

US 2023/0190978 A1 Jun. 22, 2023

(30) Foreign Application Priority Data

May 20, 2020 (GB) ..................................... 2007529

(51) Int. Cl.
*A61L 9/014* (2006.01)
*A01N 25/34* (2006.01)
(Continued)

(52) U.S. Cl.
CPC .............. *A61L 9/014* (2013.01); *A01N 25/34* (2013.01); *A01N 59/06* (2013.01); *A01N 59/16* (2013.01);
(Continued)

(58) Field of Classification Search
CPC ... A61L 9/00; A61L 9/014; A61L 2/23; A61L 2/232; A61L 2/235; A61L 2/238;
(Continued)

(56) References Cited

U.S. PATENT DOCUMENTS 4,426,462 A * 1/1984 Weissenfels .......... C08J 9/0033 521/181
2003/0084788 A1 5/2003 Fraser
(Continued)

FOREIGN PATENT DOCUMENTS

JP H09173432 A 7/1997
JP 2011000561 A 1/2011
JP 2018202356 A 12/2018

OTHER PUBLICATIONS

Search Report in the United Kingdom for Application No. GB2007529.7, dated Nov. 19, 2020.
(Continued)

*Primary Examiner* — Timothy C Cleveland
(74) *Attorney, Agent, or Firm* — Ryan T. Grace; Advent, LLP

(57) ABSTRACT

The present invention relates to open-celled phenolic foam filters. In particular, the present invention relates to open-celled phenolic foam air filters for killing microbes present in air, and the use of said filters in antimicrobial air sanitation systems.

20 Claims, 1 Drawing Sheet

(51) Int. Cl.

| | |
|---|---|
| ***A01N 59/06*** | (2006.01) |
| ***A01N 59/16*** | (2006.01) |
| ***A01N 59/20*** | (2006.01) |
| ***A01P 1/00*** | (2006.01) |
| ***B01D 39/16*** | (2006.01) |
| ***B01D 39/20*** | (2006.01) |
| ***B01D 46/00*** | (2022.01) |
| ***B01J 20/02*** | (2006.01) |
| ***B01J 20/26*** | (2006.01) |
| ***B01J 20/28*** | (2006.01) |
| ***F24F 3/167*** | (2021.01) |
| ***F24F 13/068*** | (2006.01) |

(52) U.S. Cl.

CPC ................ *A01N 59/20* (2013.01); *A01P 1/00* (2021.08); *B01D 39/1676* (2013.01); *B01D 39/2031* (2013.01); *B01D 39/2041* (2013.01); *B01D 46/0028* (2013.01); *B01J 20/0237* (2013.01); *B01J 20/262* (2013.01); *B01J 20/28026* (2013.01); *B01J 20/28035* (2013.01); *B01J 20/28045* (2013.01); *B01J 20/28069* (2013.01); *B01J 20/28085* (2013.01); *F24F 3/167* (2021.01); *F24F 13/068* (2013.01); *A61L 2209/14* (2013.01); *A61L 2209/22* (2013.01); *B01D 2239/0442* (2013.01); *B01D 2239/0478* (2013.01); *B01D 2239/1208* (2013.01); *B01D 2239/1241* (2013.01); *B01D 2279/65* (2013.01)

(58) Field of Classification Search

CPC .... A61L 2209/14; A61L 2209/22; F24F 3/16; F24F 3/167; F24F 13/068; F24F 8/10; F24F 8/108; F24F 8/15; F24F 8/20; F24F 8/24; A01P 1/00; A01N 25/34; A01N 59/00; A01N 59/06; A01N 59/16; A01N 59/20; B01D 39/1676; B01D 39/2031; B01D 39/2041; B01D 46/0028; B01D 2239/0442; B01D 2239/0478; B01D 2239/1208; B01D 2239/1241; B01D 2279/65; B01J 20/0237; B01J 20/262; B01J 20/28026; B01J 20/28035; B01J 20/208045; B01J 20/28069; B01J 20/28085

See application file for complete search history.

(56) References Cited

U.S. PATENT DOCUMENTS

| | | | | |
|---|---|---|---|---|
| 2017/0304815 | A1 | 10/2017 | Vachon | |
| 2018/0171093 | A1 | 6/2018 | Greiner et al. | |
| 2021/0331107 | A1* | 10/2021 | Holler | B32B 5/18 |

OTHER PUBLICATIONS

International Search Report and Written Opinion for Application No. PCT/EP2021/063466, dated Oct. 1, 2021.

* cited by examiner

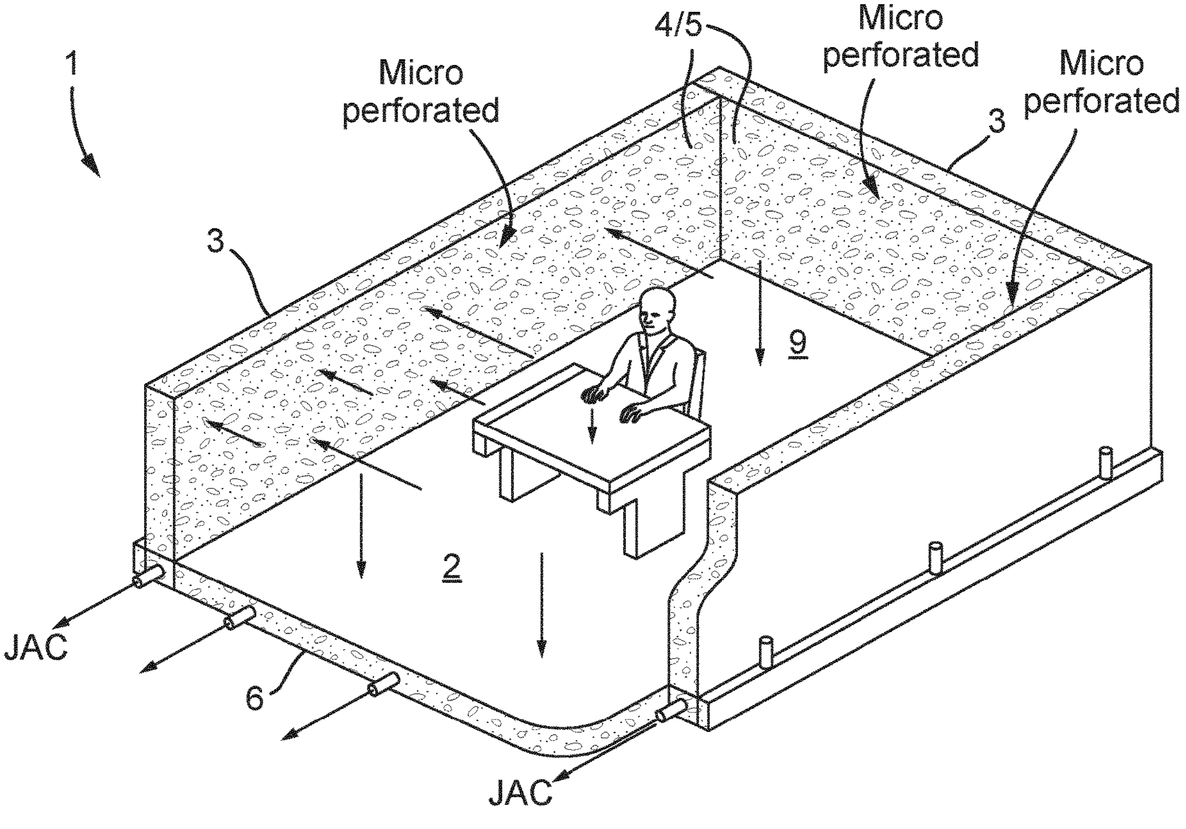
1
Micro
perforated
4/5
Micro
perforated
Micro
perforated
3
3
9
2
JAC
6
JAC

ANTI-MICROBIAL FILTER

FIELD OF THE INVENTION

The present invention relates to open-celled phenolic foam filters. In particular, the present invention relates to open-celled phenolic foam air filters for killing microbes present in air, and the use of said filters in antimicrobial air sanitation systems.

BACKGROUND TO THE INVENTION

Recently, there has been increased interest in the development of air filters for the sanitisation and cleaning of air, such as air circulating in public spaces. In 2020, the global pandemic caused by the virus SARS-CoV-2 has increased interest in the development of such filters for the effective sanitisation and cleaning of air circulating in contained spaces such as buildings and public transport etc. It is known that certain viral particles, such as SARS-CoV-2 particles present in the saliva of infected people can circulate in air when the saliva is introduced to the air as an aerosol by the coughing or sneezing of infected persons. The viral particles remain present in tiny saliva particles that are light enough to float in air currents which may transmit the viral particles to other people, thereby spreading infection. The particles also settle on surfaces which allows for transmission to persons who come into contact with those surfaces. In confined spaces such as buildings, vehicles and boats, this increases the likelihood of the virus spreading between people. It would thus be very useful if air filtration systems could be developed that effectively clean and sanitise circulating air so as to remove and/or kill microbes present in the air, thereby reducing the risk of infection spreading.

Phenolic resins are synthetic polymers obtained by the reaction of phenol or substituted phenol with formaldehyde, and are found in a myriad of industrial products. Phenolic laminates are made by impregnating one or more layers of a base material such as paper, fiberglass or cotton with phenolic resin and laminating the resin-saturated base material under heat and pressure. The resin fully polymerizes (cures) during this process forming the thermoset polymer matrix. The base material choice depends on the intended application of the finished product. Paper phenolics are used in manufacturing electrical components such as punch-through boards, in household laminates, and in paper composite panels.

Glass phenolics are particularly well suited for use in the high speed bearing market. Phenolic micro-balloons are used for density control. The binding agent in normal (organic) brake pads, brake shoes and clutch disks are phenolic resin. Synthetic resin bonded paper, made from phenolic resin and paper, is used to make countertops. Another use of phenolic resins is the making of Duroplast, used in the Trabant automobiles.

Phenolic resins are also used for making exterior plywood commonly known as weather and boil proof (WBP) plywood because phenolic resins have no melting point but only a decomposing point generally in the temperature range of 220° C. and above.

Phenolic resin is also used as a binder in loudspeaker driver suspension components which are made of cloth, and higher end billiard balls are made from phenolic resins, as opposed to the polyesters used in less expensive sets. Phenolic foams have been used for a variety of purposes such as thermal insulation panels (due to low thermal conductivity, fire safety properties and high closed-cell characteristics); construction and mining applications (due to fire-resistance, high compression strength and adaption to strata movement and closed-cell characteristics); and floral foams (due to low strength, easy cutting, easy crushability and very small pore size which allows for capillary action).

SUMMARY OF THE INVENTION

The present invention is based, in part, on the surprising finding that certain highly porous open-celled phenolic foams can act as filters for aerosol type materials such as suspensions of liquid droplets within air. Such open-celled phenolic foams additionally have antimicrobial agents that can contact microbes that may be present in saliva particles suspended within the air. As the air containing saliva particles is drawn through the open-celled phenolic foam filter, the saliva particles that may contain microbes are brought into contact with the antimicrobial agent entrained therein allowing the antimicrobial agent to kill the microbes present in the air.

The highly open-celled structure of the phenolic foam has been found essential for achieving these effects since the interconnectedness of the foam cells is necessary for the passage of air there between, and to avoid the need for high pressures to be needed. Additionally, the open-celled foams provide a tortuous path for the passage of air therethrough, due to the nature of interconnections between adjacent foam cells. This means that a given portion of air does not travel in a straight direction through the foam filter, rather it travels a considerable distance (and across a great surface area within the foam) inside the filter relative to the dimensions of the filter itself. This causes a given portion of air to be exposed to a greater amount of antimicrobial agent. This combination of features has been found to provide improved filtration of air, and improved killing of any microbes within the air.

An open-celled structure with a particular accessible pore volume has also been found to be important since it allows air to be drawn through the foam filter by application of only a low pressure vacuum. Smaller accessible pore volumes either do not allow for air to be drawn through the foam, or at least require far higher pressures to do so.

According to a first aspect of the invention, there is thus provided a foam filter for filtering air comprising an open-celled phenolic foam, the open-celled phenolic foam having an accessible pore volume of from 0.50 $m^3$ to 0.96 $m^3$ per $m^3$ of foam, and further comprising an antimicrobial agent.

Preferably, the antimicrobial agent is entrained within the polymer matrix of the foam. However, in alternative embodiments, the antimicrobial agent is present as a coating on the inner surfaces of the pores of the foam. In an embodiment, the antimicrobial agent present as a coating on the inner surfaces of the foam may be applied by a vapour deposition process.

Preferably, the anti-microbial agent comprises a finely divided particulate solid having antimicrobial properties. Alternatively or in addition, the anti-microbial agent may comprise a fibre-containing material with antimicrobial properties, such as antimicrobial fibrous materials.

Typically, the open-celled phenolic foam comprises cells having an average cell size of from 0.5 mm to 7 mm. Typically, 50% or more of the cells present in the phenolic foam have a cell size of from 0.5 mm to 7 mm. Preferably, 70% or more of the cells present in the phenolic foam have a cell size of from 0.5 mm to 7 mm. More preferably, 80% or more of the cells present in the phenolic foam have a cell size of from 0.5 mm to 7 mm.

Preferably, the open-celled phenolic foam comprises cells having an average cell size of from 3 mm to 6 mm. Preferably, 50% or more of the cells present in the phenolic foam have a cell size of from 3 mm to 6 mm. More preferably, 70% or more of the cells present in the phenolic foam have a cell size of from 3 mm to 6 mm. Most preferably, 80% or more of the cells present in the phenolic foam have a cell size of from 3 mm to 6 mm.

Preferably, the open-celled phenolic foam is rigid.

Preferably, the open-celled phenolic foam has a density of from 80 kg/m$^3$ to 800 kg/m$^3$, preferably from 100 kg/m$^3$ to 500 kg/m$^3$, more preferably from 120 kg/m$^3$ to 400 kg/m$^3$, and most preferably from 120 kg/m$^3$ to 350 kg/m$^3$.

Preferably, the open-celled phenolic foam has an accessible pore volume of from 0.6 m$^3$ to 0.95 m$^3$ per m$^3$ of foam. The reference to accessible pore volume intended to refer to the pores of the open-celled foam which can be accessed (i.e. through which air may be drawn) during use of the filter.

Preferably, where the antimicrobial agent is in the form of a particle or fibre, it is present in the open-celled phenolic foam in an amount of from 5% by weight to 50% by weight of the foam material.

However, it will be appreciated that should the antimicrobial agent be in the form of a much smaller structure, such as a nano-particle, it can be present in much smaller amounts.

Preferably, the antimicrobial agent is substantially uniformly dispersed throughout the foam material. This is especially preferred where the antimicrobial agent comprises a finely divided particulate solid.

Where the antimicrobial agent comprises a finely divided particulate solid having antimicrobial properties, preferably, the finely divided particulate solid has an average particle size of from 0.2 to 800 μm, preferably from 1 to 100 μm and most preferably from 10 to 50 μm.

The antimicrobial agent can be an antibacterial agent, an antiviral agent, or a combination thereof. Preferably, the antimicrobial agent is an antiviral agent. More preferably, the antiviral agent is viricidal against coronaviruses, and most preferably, the antiviral agent is viricidal against the virus SARS-CoV-2.

Typically, the antimicrobial agent comprises finely divided particulate solid having antimicrobial properties comprising metal particles, preferably wherein the metal particles comprise copper, titanium, silver, aluminium, cobalt, zinc, zirconium, molybdenum, tin or lead. Most preferably, the finely divided particulate solid having antimicrobial properties comprises copper particles.

Preferably, at least a portion of the antimicrobial agent is present at a surface of the open-celled phenolic foam, such as within the pores of the foam. In addition, where the antimicrobial agent comprises fibre-containing material with antimicrobial properties, the fibres may extend into the pores of the open-celled foam. According to a second aspect of the invention, there is provided a laminated filter structure comprising a foam filter according to any one of the preceding claims, and at least one layer of additional material in contact with at least one surface of the foam filter, preferably, wherein the at least one layer of additional material is bonded to the at least one surface of the foam filter, wherein:

(i) the at least one layer of additional material forms a portion of an outer surface of the structure, wherein the at least one layer of additional material does not cover the entirety of the at least one surface of the foam filter such that a portion of the at least one surface of the foam filter is exposed as a portion of the outer surface of the structure; or (ii) the at least one layer of additional material comprises at least one aperture extending therethrough between the at least one surface of the foam filter and an outer surface of the at least one layer of additional material, wherein the outer surface of the at least one layer of additional material forms the outer surface of the structure.

Preferably, the at least one layer of additional material comprises at least one skin of sheet-form material.

Preferably, the laminated filter structure comprises a laminated filter panel.

Preferably, the laminated structure comprises a laminated filter panel comprising a foam filter according to the first aspect of the invention, and at least one skin of sheet-form material bonded to at least one surface of the foam filter, wherein:

(i) the at least one skin of sheet-form material forms a portion of an outer surface of the panel, wherein the at least one skin of sheet-form material does not cover the entirety of the at least one surface of the foam filter such that a portion of the at least one surface of the foam filter is exposed as a portion of the outer surface of the panel; or (ii) the at least one skin of sheet-form material comprises at least one aperture extending therethrough between the at least one surface of the foam filter and an outer surface of the at least one skin of sheet-form material, wherein the outer surface of the at least one skin of sheet-form material forms the outer surface of the panel.

More preferably, the at least one layer of additional material such as the at least one skin of sheet-form material comprises a plurality of apertures therein, wherein the plurality of apertures extend through the at least one layer of additional material between the at least one surface of the foam filter and an outer surface of the at least one layer of additional material.

Preferably, the plurality of apertures comprises a plurality of perforations, such as micro-sized perforations or macro-sized perforations The plurality of micro-size perforations may have a diameter of from 0.05 mm to 1 mm, such as 0.075 to 0.5 mm, for example about 0.1 mm to 0.25 mm. The macro-sized perforations may have a diameter of from 1.25 mm to 5 mm, such as 1.5 to 3 mm.

Preferably, a further layer of additional material such as a skin of sheet-form material is bonded to an opposing surface of the foam filter, such that the foam filter is sandwiched between the layers of additional material such as the skins of sheet-form material.

Preferably, the at least one skin of sheet-form material comprises a thermoset material, optionally wherein the thermoset material further comprises carbon fibres, glass fibres, aramid fibres, metallic fibres or any combination thereof. More preferably, the skin of sheet-form material comprises a thermoset material comprising glass fibres.

Preferably, the thermoset material comprises SMC (sheet moulding compound), BMC (bulk moulding compound), or AMC (such as described in WO2018/220383).

AMC is a product obtainable by curing an uncured material for forming a phenolic resin sheet, wherein the uncured material comprises: uncured phenolic resin; filler; a catalyst in an amount of less than 2 wt. % relative to the content of phenolic resin; and wherein the filler is present in a ratio of filler to uncured phenolic resin in an amount of 2.5:1 and greater, and further wherein the filler comprises a transition metal hydroxide and/or aluminium hydroxide in a ratio of metal hydroxide to uncured phenolic resin in an amount of 1:1.5 to 3:1. Preferably, the catalyst is present in an amount of less than 1 wt. % relative to the content of the uncured phenolic resin. Preferably, the phenolic resin is a phenol-formaldehyde resin. Preferably, the filler is a particulate solid which is insoluble in the uncured material such as an inorganic material selected from one or more of clays, clay minerals, talc, vermiculite, gypsum, metal oxides, refractories, solid or hollow glass microspheres, fly ash, coal dust, wood flour, grain flour, nut shell flour, silica, ground plastics and resins in the form of powder, powdered reclaimed waste plastics, powdered resins, pigments, starches, or other suitable powdered natural material. Preferably, the transition metal or aluminium hydroxides are of formula $M(OH)_3$, wherein M is a metal, and more preferably, the metal M may be selected from one or more of scandium, vanadium, chromium, manganese, iron, cobalt and aluminium. Preferably, the metal hydroxide is aluminium hydroxide. Preferably, the material further comprises a viscosity controlling agent. In a highly preferable embodiment, the uncured material further comprises fibres such as glass fibres, carbon fibres, metal fibres and aramid fibres, optionally in the form of a layer such as a mat or fabric.

Preferably, the at least one layer of additional material is non-porous, especially on the opposing surface.

Preferably, the material of the at least one skin of sheet-form material is mechanically keyed with the at least one surface of the foam filter, or wherein the at least one skin of sheet-form material is adhered to the at least one surface of the foam filter, such as by an adhesive (such as described in WO2019/229436). Such an adhesive comprises (i) 1 part by weight of a phenolic resin; (ii) from 2 to 4 parts by weight of a transition metal hydroxide and/or aluminium hydroxide; and (iii) from 0.2 to 1 parts by weight, preferably from 0.4 to 0.9 parts by weight of a viscosity controlling agent. Preferably, the adhesive comprises the adhesive comprises from 2.5 to 3.5 parts by weight of the metal hydroxide. Preferably, the viscosity controlling agent is a liquid, preferably selected from one or more of butanol, chloroform, ethanol, water, acetonitrile, hexane and isopropyl alcohol. Preferably, the phenolic resin is a phenolic resole resin, preferably a phenolic resole resin that includes less than 10% by weight of free formaldehyde, preferably less than 1% by weight, more preferably less than 0.5% by weight, for example less than 0.1% by weight. Preferably, the metal hydroxide comprises particles having a particle size distribution with a D90 from 50 to 70 μm, and/or a D50 from 15 to 35 μm, and/or a D10 from 1 to 10 μm. Preferably, the adhesive further comprises fibres such as woven or unwoven fibres. Preferably, the fibres are in the form of a layer.

More preferably, the material of the at least one skin of sheet-form material is mechanically keyed with the at least one surface of the foam filter, and wherein the sheet-form material extends into the cells of the open-celled phenolic foam.

Preferably, the laminated filter structure is obtained or obtainable by a curing process comprising the steps of: providing a sheet-form curable material; providing a foam filter, and pressing the sheet-form material to the foam filter; and optionally wherein gas and/or vapour can be displaced from the pressing region through the foam filter.

Preferably, the foam filter comprises one or more grooves, channels, hollows or indentations so as to improve the flow of air through the laminated filter structure.

Preferably, the at least one layer of additional material comprises one or more grooves, channels, hollows or indentations within its outer surface, such that an outer surface of the structure comprises one or more grooves, channels or indentations therein. More preferably, the one or more grooves, channels, hollows or indentations comprise at least one aperture therein extending between the at least one surface of the foam filter and an outer surface of the at least one layer of additional material.

Preferably, the one or more grooves, channels, hollows or indentations are configured so as to direct saliva particles present in air towards the at least one aperture.

In some embodiments, the at least one layer of additional material comprises an anti-microbial coating on its outer surface, such that the antimicrobial coating is disposed upon a portion of the outer surface of the filter structure. Preferably, the antimicrobial coating comprises an anti-bacterial coating or an antiviral coating, such as an agent that is viricidal against the virus SARS-CoV-2. More preferably, the antimicrobial coating comprises finely divided particulate metal particles. Alternatively or additionally, the at least one layer of additional material comprises an antimicrobial agent (such as those discussed above) dispersed within.

According to a third aspect of the invention, there is provided a system for the sanitisation of air, wherein the system comprises:

(i) a chamber comprising one or more foam filters according to the first aspect of the invention, or laminated filter structures according to the second aspect of the invention within the chamber, wherein the one or more foam filters or one or more laminated filter structures are in fluid communication with an interior of the chamber;

(ii) one or more conduits configured for drawing air from an interior of the chamber, through the one or more foam filters or one or more laminated filter structures and into the one or more conduits; and optionally (iii) means for actively replacing the air drawn from the interior of the chamber with additional air.

Preferably, the means for actively replacing the air drawn from the interior of the chamber with additional air, comprises a conduit configured to draw air from the exterior of the chamber to the interior of the chamber. More preferably, the means for actively replacing the air drawn from the interior of the chamber is configured to introduce filtered or sanitised air to the interior of the chamber.

Preferably, the means for actively replacing the air drawn from the interior is configured to operate so as to keep the air pressure in the interior of the chamber at a constant, or near constant value, preferably wherein the value is atmospheric pressure. In an embodiment, the means for actively replacing the air drawn from the interior is configured to operate so as to reduce the air pressure in the interior of the chamber.

In an embodiment, the one or more foam filters or one or more filter structures are a component of one or more walls of the chamber; one or more doors of the chamber, if present; the floor or ceiling of the chamber; structural feature, if present; furniture within the chamber, if present or any combination thereof. Preferably, the one or more filter structures are a component of one or more walls of the chamber, or the floor of the chamber.

Preferably, the means for actively replacing the air drawn from the interior is in fluid communication with an aperture present in the ceiling of the chamber.

In an embodiment, the means for replacing the air drawn from the interior of the chamber with additional air comprises a pump, such as a pump configured to direct air into the chamber. Preferably, the system of the invention is configured so as to minimise or eliminate horizontal air currents within the chamber. More preferably, the means for replacing the air drawn from the interior of the chamber with additional air comprises a conduit configured to draw air from the exterior of the chamber to the interior of the chamber, wherein said conduit is in fluid communication with an aperture in the ceiling of the chamber, and wherein the one or more foam filters or one or more filter structures are a component of one or more walls of the chamber, or the floor of the chamber.

In an embodiment, the means for replacing the air drawn from the interior of the chamber with additional air comprises one or more foam filters according to the first aspect of the invention or one or more filter structures according to the second aspect of the invention, wherein the one or more foam filters or one or more filter structures are a component of the walls or ceiling of the chamber; and wherein the means for replacing the air drawn from the interior of the chamber with additional air is configured to direct air from outside the chamber, through the one or more foam filters or one or more filter structures and into the interior of the chamber.

According to a fourth aspect of the invention, there is provided a method of sanitising air with a system according to the third aspect of the invention, wherein the method comprises drawing the air from the interior of a chamber through one or more foam filters according to the first aspect of the invention or one or more laminated filter structures according to the third aspect of the invention, and into the one or more conduits configured for drawing air from the interior of the chamber; and optionally wherein the method further comprises replacing the air drawn from the interior of the chamber with additional air.

Preferably, the method comprises removing and/or killing viruses or bacteria present in the air with the one or more structures or foam filters, such as SARS-CoV-2.

Preferably, the method further comprises replacing the air drawn from the interior of the chamber with clean sanitised air, and/or wherein the method comprises maintaining the air pressure of the interior of the chamber at or near to atmospheric pressure and/or wherein the method comprises increasing the air pressure of the interior of the chamber.

In an embodiment, horizontal air currents within the chamber are eliminated or minimised. Preferably, the one or more foam filters or one or more filter panels are situated within the floor, furniture and/or walls of the chamber, and the means for replacing air drawn from the interior of the chamber with additional air are in fluid communication with an aperture in the ceiling of the chamber.

According to a fifth aspect of the invention, there is provided the use of a foam filter according to the first aspect of the invention; a laminated filter structure according to the second aspect of the invention; or a system according to the third aspect of the invention for killing microbes present in air and/or sanitising air.

Preferably, the microbes comprise bacteria or viruses, such as SARS-CoV-2.

Preferably, the use comprises drawing the microbes present in the air into contact with the open-celled phenolic foam of the filter or filter panel.

According to a sixth aspect of the invention, there is provided the use of a system of the third aspect of the invention, for controlling the flow of air into and out of a chamber in the event of a fire.

Preferably, the use comprises sealing the chamber such that the only passage of air into and out of the chamber is via the one or more conduits configured for drawing air from an interior of the chamber, through the one or more foam filters or the one or more filter structures and into the one or more conduits; and the means for replacing the air drawn from the interior of the chamber with additional air.

According to a sixth aspect of the invention, there is provided a kit for forming a chamber, or a component of a chamber, wherein the kit comprises a foam filter according to the first aspect of the invention, or a laminated filter structure according to the second aspect of the invention; optionally one or more further components for forming the chamber or component of a chamber; and optionally instructions for assembling the chamber or component of a chamber with the foam filter or laminated structure and optional one or more further components.

Preferably, the chamber is as defined above in accordance with the third aspect of the invention.

BRIEF DESCRIPTION OF THE DRAWINGS

FIG. 1 is a sketch of a system of the invention, configured within a room of a building.

DETAILED DESCRIPTION OF THE INVENTION

It has been appreciated by the inventors of the present invention that certain highly porous, open-celled phenolic foams have various properties that render them useful as air filters. It has been found that air can be drawn through certain foams through the pore structures of the foams by application of a pressure gradient such as suction. It has also been found possible to disperse antimicrobial agents within the phenolic foams. Air that contains pathogenic microbes, such as pathogenic microbes present in small saliva particles suspended in the air can be drawn by pressure such as a suction force through the pore structure of the phenolic foam filter where the microbes present in the saliva particles encounter the antimicrobial agent present in the foam. The antimicrobial agent kills the microbes present in the saliva particles. Air eventually exits the phenolic foam filter with no microbes, only dead microbes, or a reduced population of alive microbes present therein. Whilst the foam filters of the invention are preferably adapted so as to bring the antimicrobial agent present therein into contact with pathogenic microbes present in saliva particles suspended in air, it will be understood that the presence of saliva particles in the air is not essential, and that the foam filters of the invention can also kill microbes that are directly dispersed within air, without being present in saliva particles.

Phenolic Foam Filters

The highly open-celled porous foams of the present invention can be prepared using the method described herein.

It has been found essential that the phenolic foam filters have a highly open-celled structure. The term open-celled structure is used to refer to polymer foams that have intercommunicating gas cells. This has been found essential so that air can successively pass through the polymer foam filter, and via the gaps between them. If the foam had a closed-cell structure, or only a partially open-celled structure instead, then it would not be possible to pass air effectively through the filter.

The foam filters of the invention have an accessible pore volume of from 0.5 $m^3$ to 0.96 $m^3$ per $m^3$ of foam, and preferably from 0.6 $m^3$ to 0.95 $m^3$ per $m^3$ of foam. Such an accessible pore volume is essential for the successful passage of air through the foam enabling the foam to successfully act as a filter. If the accessible pore volume is smaller, than air flow through the foam is not possible, or at least overly restricted such that significant volumes of air cannot be filtered. In such a case, excessive force or pressure gradients may be required in order to drive air through the foam filter. This is undesirable from an economic perspective, and is also impractical. If the accessible pore volume of the foam filters are larger than the above-described amount, then desirable physical properties of the foam such as durability and strength are compromised. This is undesirable when the foam filter is included as a component in, for example, a wall or floor of a building where it may be desirable for the foam filter to also have some degree of structural integrity.

The term accessible pore volume as used herein, is a term of art used to refer to the volume space that is accessible to a medium (such as air) accessing the internal pore structure of the polymer foam. Accessible pore volume of an open-celled phenolic foam resin may be determined by standard methods known in the art such as mercury intrusion porosimetry.

The phenolic foam filters preferably have an average pore size of from 0.5 mm to 7 mm and preferably from 3 mm to 6 mm. The term "average pore size" as used herein is intended to mean the mean pore diameter of the pores within the foam, and may be determined by standard techniques known in the art.

The phenolic foam filters preferably have a volume and internal surface area that render the foam suitable for successfully filtering air in the manner discussed above, and killing all microbes contained therein. An advantage of the filters of the invention is that they can be made with a wide variety of dimensions and still successfully filter air. For example, a panel that is very long and wide, but not particularly thick (e.g. 50 mm×1 m×1 m) can be configured such that air is drawn into one part of the filter, and has to pass through a whole length or width of the panel before it reaches, for example, a conduit attached to a vacuum pump that is drawing air through the filter. In such a scenario, the air still passes through a large surface area of the foam. Accordingly, provided that a sufficient total volume and surface area of the filter foam are used, filters with many different dimensions can be used, provided the filters are configured so that the air passes through the necessary surface area of pores. Typically, the filter also has dimensions suitable for inclusion in a structure such as a panel that can be included in the wall, floor, ceiling or door of a room, or in furniture, as discussed in greater detail below.

The antimicrobial agent can be any suitable antimicrobial agent that can effectively kill or inhibit the pathogenicity of microbes such as viruses and bacteria. Preferably, the antimicrobial agent is an antiviral agent such an agent that is viricidal against SARS-CoV-2.

As discussed above, in preferable embodiments, the antimicrobial agent comprises a finely divided particulate solid having antimicrobial properties. Such antimicrobial agents are particularly useful since they can be easily substantially uniformly dispersed throughout the foam material, meaning that all sections of the polymer foam material are antimicrobial which leads to an improved filtration and sanitation of the air, since less air passes through the foam without contacting the antimicrobial agent. Examples of finely divided particulate materials (including nano-particles) that can be used include metals such as metal powder with antimicrobial properties such as copper, titanium, silver, aluminium, cobalt, zinc, zirconium, molybdenum, tin or lead. However, it will be understood that other antimicrobial particulates and powders can be included in the foam filters of the invention. Copper powder (including nano-particles) is particularly preferred since it has recently been found that copper is viricidal against the SARS-CoV-2 virus.

In alternative embodiments, or in addition, the antimicrobial agents comprise fibre-containing materials such as antimicrobial fibrous materials. Fibre-containing materials may be useful since when present in the polymer foam matrix, they may be present at the surfaces of the pores of the matrix such that they are well placed for contacting air, saliva particles and microbes passing through the pores of the foam filter. Examples of suitable fiber-containing antimicrobial agents include metal fibres, such as fibres of the antimicrobial metals discussed above Where the antimicrobial agent comprises a finely divided particulate solid having antimicrobial properties, the finely divided particulate solid having antimicrobial properties typically has an average particle size of from 0.2 to 800 μm, preferably from 1 to 100 μm and most preferably from 10 to 50 μm. Average particle size can be determined according to methods known in the art, such as ASTM B330-15.

A particular advantage associated with the use of metallic antimicrobial agents, such as those discussed above, is that due to the substantially uniform dispersal of the antimicrobial agents within the foam, the foam may be rendered electrically conductive. Electrically conductive foam can be desirable for a variety of reasons, for example, transmitting electricity between various electronic components in the chamber, or between an electrical component in the chamber and an external source of electricity. In particular, electrically conductive foam can be used to provide heating to the chamber.

This can be advantageous as it allows the foam to conduct

The foam filters of the invention can be prepared using the methods described herein.

One particularly suitable method that can be used to form foam filters of the invention, is as follows.

A curing reaction can be affected between:

(a) a liquid phenolic resole having a reactivity number (as defined below) of at least 1; and (b) a strong acid hardener for the resole, in the presence of:

(c) a finely divided inert and insoluble particulate solid which is present in an amount of at least 5% by weight of the liquid resole and is substantially uniformly dispersed through the mixture containing resole and hardener; the temperature of the mixture containing resole and hardener due to applied heat not exceeding 85° C. and the said temperature and the concentration of the acid hardener being such that compounds generated as by-products of the curing reaction are volatilised within the mixture before the mixture sets whereby a foamed phenolic resin product is produced.

By a phenolic resole is meant a solution in a suitable solvent of the acid-curable prepolymer composition obtained by condensing, usually in the presence of an alkaline catalyst such as sodium hydroxide, at least one phenolic compound with at least one aldehyde, in well-known manner. Examples of phenols that may be employed are phenol itself and substituted, usually alkyl substituted, derivatives thereof provided that the three positions on the phenolic benzene ring o- and p- to the phenolic hydroxyl group are unsubstituted. Mixtures of such phenols may also be used. Mixtures of one or more than one of such phenols with substituted phenols in which one of the ortho or para positions has been substituted may also be employed where an improvement in the flow characteristics of the resole is required but the cured products will be less highly cross-linked. However, in general, the phenol will be comprised mainly or entirely of phenol itself, for economic reasons.

The aldehyde will generally be formaldehyde although the use of higher molecular weight aldehydes is not excluded.

The phenol/aldehyde condensation product component of the resole is suitably formed by reaction of the phenol with at least 1 mole of formaldehyde per mole of the phenol, the formaldehyde being generally provided as a solution in water, for example as formalin. It is preferred to use a molar ratio of formaldehyde to phenol of at least 1.25 to 1 but ratios above 2.5 to 1 are preferably avoided. The most preferred range is 1.4 to 2.0 to 1.

The mixture may also contain a compound having two active H atoms (dihydric compound) that will react with the phenol/aldehyde reaction product of the resole during the curing step to reduce the density of cross-linking. Preferred dihydric compounds are diols, especially alkylene diols or diols in which the chain of atoms between the OH groups contains not only methylene and/or alkyl-substituted methylene groups but also one or more hetero atoms, especially oxygen atoms, for example ethylene glycol, propylene glycol, propane-1,3-diol, butane-1,4-diol and neopentyl glycol. Particularly preferred diols are poly-, especially di-, (alkylene ether) diols for example diethylene glycol and, especially, dipropylene glycol. Preferably the dihydric compound is present in an amount of from 0 to 35% by weight, more preferably 0 to 25% by weight, based on the weight of phenol/aldehyde condensation product Most preferably, the dihydric compound, when used, is present in an amount of from 5 to 15% by weight based on the weight of phenol/aldehyde condensation product. When such resoles containing dihydric compounds are employed in the present process, products having a particularly good combination of physical properties, especially strength, can be obtained.

Suitably, the dihydric compound is added to the formed resole and preferably has 2 to 6 atoms between OH groups.

The resole may comprise a solution of the phenol/aldehyde reaction product in water or in any other suitable solvent or in a solvent mixture, which may or may not include water. Where water is used as the sole solvent, it is preferred to be present in an amount of from 15 to 35% by weight of the resole, preferably 20 to 30%. Of course the water content may be substantially less if it is used in conjunction with a co solvent, for example an alcohol or one of the above-mentioned dihydric compounds where one is used.

As indicated above, the liquid resole (i.e. the solution of phenol/aldehyde product optionally containing dihydric compound) must have a reactivity number of at least 1. The reactivity number is 10/x where x is the time in minutes required to harden the resole using 10% by weight of the resole of a 66 to 67% aqueous solution of p-toluene sulfonic acid at 60° C. The test involves mixing about 5 ml of the resole with the stated amount of the p-toluene sulfonic acid solution in a test tube, immersing the test tube in a water bath heated to 60° C. and measuring the time required for the mixture to become hard to the touch. The resole should have a reactivity number of at least 1 for useful foamed products to be produced and preferably the resole has a reactivity number of at least 5, most preferably at least 10.

The pH of the resole, which is generally alkaline, is preferably adjusted to about 7, if necessary, for use in the process, suitably by the addition of a weak organic acid such as lactic acid.

Examples of strong acid hardeners are inorganic acids such as hydrochloric acid, sulphuric acid and phosphoric acid, and strong organic acids such as aromatic sulphonic acids, for example toluene sulphonic acids, and trichloroacetic acid. Weak acids such as acetic acid and propionic acid are generally not suitable. The preferred hardeners for the process of the invention are the aromatic sulfonic acids, especially toluene sulfonic acids.

The acid may be used as a solution in a suitable solvent such as water.

When the mixture of resole, hardener and solid is to be poured, for example into a mould and in slush moulding applications, the amount of inert solid that can be added to the resole and hardener is determined by the viscosity of the mixture of resole and hardener in the absence of the solid. For these applications, it is preferred that the hardener is provided in a form, for example solution, such that when mixed with the resole in the required amount yields a liquid having an apparent viscosity not exceeding about 50 poises at the temperature at which the mixture is to be used, and the preferred range is 5 to 20 poises. Below 5 Poises, the amount of solvent present tends to present difficulties during the curing reaction.

The curing reaction is exothermic and will therefore of itself cause the temperature of the mixture containing resole and acid hardener to be raised. The temperature of the mixture may also be raised by applied heat but the temperature to which said mixture may then be raised (that is, excluding the effect of any exotherm) must not exceed 85° C.

If the temperature of the mixture exceeds 85° C. before addition of the hardener, it is difficult or impossible thereafter to properly disperse the hardener through the mixture because of incipient curing. On the other hand, it is difficult, if not impossible, to uniformly heat the mixture above 85° C. after addition of the hardener.

Increasing the temperature towards 85° C. tends to lead to coarseness and non-uniformity of the texture of the foam but this can be offset at least to some extent at moderate temperatures by reducing the concentration of hardener. However at temperatures much above 75° C. even the minimum amount of hardener required to cause the composition to set is generally too much to avoid these disadvantages. Thus, temperatures above 75° C. are preferably avoided and preferred temperatures for most applications are from ambient temperature to about 75° C. The preferred temperature range appears to depend to some extent on the nature of the solid (c). For most solids it is from 25 to 65° C. but for some solids, in particular wood flour and grain flour, the preferred range is 25 to 75° C. The most preferred temperature range is 30 to 50° C. Temperatures below ambient, for example down to 10° C. can be used, if desired, but no advantage is gained thereby. In general, at temperatures up to 75° C., increase in temperature leads to decrease in the density of the foam and vice versa.

The amount of hardener present also affects the nature of the product as well as the rate of hardening. Thus, increasing the amount of hardener not only has the effect of reducing the time required to harden the composition but above a certain level dependant on the temperature and nature of the resole it also tends to produce a less uniform cell structure. It also tends to increase the density of the foam because of the increase in the rate of hardening. In fact, if too high a concentration of hardener is used, the rate of hardening may be so rapid that no foaming occurs at all and under some conditions the reaction can become explosive because of the build up of gas inside a hardened shell of resin. The appropriate amount of hardener will depend primarily on the temperature of the mixture of resole and hardener prior to the commencement of the exothermic curing reaction and the reactivity number of the resole and will vary inversely with the chosen temperature and the reactivity number. The preferred range of hardener concentration is the equivalent of 2 to 20 parts by weight of p-toluene sulfonic acid per 100 parts by weight of phenol/aldehyde reaction product in the resole assuming that the resole has a substantially neutral reaction, i.e. a pH of about 7. By equivalent to p-toluene sulfonic acid, we mean the amount of chosen hardener required to give substantially the same setting time as the stated amount of p-toluene sulfonic acid. The most suitable amount for any given temperature and combination of resole and finely divided solid is readily determinable by simple experiment. Where the preferred temperature range is 25 to 75° C. and the resole has a reactivity number of at least 10, the best results are generally obtained with the use of hardener in amounts equivalent to 3 to 10 parts of p-toluene sulfonic acid per 100 parts by weight of the phenol/aldehyde reaction product. For use with temperatures below 25° C. or resoles having a reactivity number below 10, it may be necessary to use more hardener.

It may be necessary to make some adjustment of the hardener composition in accordance with the nature, especially shape and size, of the mould and this can be established by experiment.

By suitable control of the temperature and of the hardener concentration, the time lapse between adding the hardener to the resole and the composition becoming hard (referred to herein as the setting time) can be varied at will from a few seconds to up to an hour or even more, without substantially affecting the density and cell structure of the product.

Another factor that controls the amount of hardener required can be the nature of the inert solid. Very few are exactly neutral and if the solid has an alkaline reaction, even if only very slight, more hardener may be required because of the tendency of the filler to neutralize it. It is therefore to be understood that the preferred values for hardener concentration given above do not take into account any such effect of the solid. Any adjustment required because of the nature of the solid will depend on the amount of solid used and can be determined by simple experiment.

The exothermic curing reaction of the resole and acid hardener leads to the formation of by-products, particularly aldehyde and water, which are at least partially volatilised.

The curing reaction is typically effected in the presence of a finely divided inert and insoluble particulate solid which is substantially uniformly dispersed throughout the mixture of resole and hardener. By an inert solid we mean that in the quantity it is used it does not prevent the curing reaction.

It is believed that the finely divided particulate solid provides nuclei for the gas bubbles formed by the volatilisation of the small molecules, primarily $CH_2O$ and/or $H_2O$, present in the resole and/or generated by the curing action, and provides sites at which bubble formation is promoted, thereby assisting uniformity of pore size. The presence of the finely divided solid may also promote stabilization of the individual bubbles and reduce the tendency of bubbles to agglomerate and eventually cause likelihood of bubble collapse prior to cure. The phenomenon may be similar to that of froth flotation employed in the concentration of low-grade ores in metallurgy. In any event, the presence of the solid is essential to the formation of the product To achieve the desired effect, the solid should be present in an amount of not less than 5% by weight based on the weight of the resole.

Any finely divided particulate solid that is insoluble in the reaction mixture is suitable, provided it is inert. The fillers may be organic or inorganic (including metallic), and crystalline or amorphous. Even fibrous solids have been found to be effective, although not preferred. Examples include clays, clay minerals, talc, vermiculite, metal oxides, refractories, solid or hollow glass microspheres, fly ash, coal dust, wood flour, grain flour, nut shell flour, silica, mineral fibres such as finely chopped glass fibre and finely divided asbestos, chopped fibres, finely chopped natural or synthetic fibres, ground plastics and resins whether in the form of powder or fibres, for example reclaimed waste plastics and resins, pigments such as powdered paint and carbon black, and starches.

Solids having more than a slightly alkaline reaction, for example silicates and carbonates of alkali metals, are preferably avoided because of their tendency to react with the acid hardener. Solids such as talc, however, which have a very mild alkaline reaction, in some cases because of contamination with more strongly alkaline materials such as magnesite, are acceptable.

Some materials, especially fibrous materials such as wood flour, can be absorbent and it may therefore be necessary to use generally larger amounts of these materials than non-fibrous materials, to achieve valuable foamed products.

The solids preferably have a particle size in the range 0.5 to 800 microns. If the particle size is too great, the cell structure of the foam tends to become undesirably coarse. On the other hand, at very small particle sizes, the foams obtained tend to be rather dense. The preferred range is 1 to 100 microns, most preferably 2 to 40 microns. Uniformity of cell structure appears to be encouraged by uniformity of particle size. Mixtures of solids may be used if desired.

If desired, solids such as finely divided metal powders may be included which contribute to the volume of gas or vapour generated during the process. If used alone, however, it be understood that the residues they leave after the gas by decomposition or chemical reaction satisfy the requirements of the inert and insoluble finely divided particulate solid required by the process of the invention.

Preferably, the finely divided solid has a density that is not greatly different from that of the resole, so as to reduce the possibility of the finely divided solid tending to accumulate towards the bottom of the mixture after mixing.

One class of solids is the hydraulic cements, for example gypsum and plaster, but not Portland cement because of its alkalinity. These solids will tend to react with water present in the reaction mixture to produce a hardened skeletal structure within the cured resin product. Moreover, the reaction with the water is also exothermic and assists in the foaming and curing reaction. Foamed products obtained using these materials have particularly valuable physical properties. Moreover, when exposed to flame even for long periods of time they tend to char to a brick-like consistency that is still strong and capable of supporting loads. The products also have excellent thermal insulation and energy absorption properties. The preferred amount of inert particulate solid is from 20 to 300 parts by weight per 100 parts by weight of resole.

Another class of solids that is preferred because its use yields products having properties similar to those obtained using hydraulic cements comprises talc and fly ash. The preferred amounts of these solids are also 20 to 200 parts by weight per 100 parts by weight of resole. For the above classes of solid, 50 to 150 parts per 100 parts of resole may be used.

Thixotropic foam-forming mixtures can be obtained if a very finely divided solid such as Aerosil (finely divided silica) is included.

In general, the maximum amount of solid that can be employed is controlled only by the physical problem of incorporating it into the mixture and handling the mixture. In general it is desired that the mixture is pourable but even at quite high solids concentrations, when the mixture is like a dough or paste and cannot be poured, foamed products with valuable properties can be obtained.

In general, it is preferred to use the fibrous solids only in conjunction with a non-fibrous solid since otherwise the foam texture tends to be poorer.

Other additives may be included in the foam-forming mixture; for example surfactants, such as anionic materials such as sodium salts of long chain alkyl benzene sulfonic acids, non-ionic materials such as those based on poly (ethylene oxide) or copolymers thereof, and cationic materials such as long chain quaternary ammonium compounds or those based on polyacrylamides; viscosity modifiers such as alkyl cellulose especially methyl cellulose, and colorants such as dyes or pigments. Plasticisers for phenolic resins may also be included provided the curing and foaming reactions are not suppressed thereby, and polyfunctional compounds other than the dihydric compounds referred to above may be included which take part in the cross-linking reaction which occurs in curing; for example di- or poly-amines, di- or poly-isocyanates, di- or poly-carboxylic acids and aminoalcohols.

Polymerisable unsaturated compounds may also be included possibly together with free-radical polymerisation initiators that are activated during the curing action for example acrylic monomers, so-called urethane acrylates, styrene, maleic acid and derivatives thereof, and mixtures thereof.

Other resins may be included for example as prepolymers which are cured during the foaming and curing reaction or as powders, emulsions or dispersions. Examples are polyacetals such as polyvinyl acetals, vinyl polymers, olefin polymers, polyesters, acrylic polymers and styrene polymers, polyurethanes and prepolymers thereof and polyester prepolymers, as well as melamine resins, phenolic novolaks, etc.

Conventional blowing agents may also be included to enhance the foaming reaction, for example low boiling organic compounds or compounds which decompose or react to produce gases.

The foam-forming compositions may also contain dehydrators, if desired.

A preferred method of forming the foam-forming composition comprises first mixing the resole and inert filler to obtain a substantially uniform dispersion of the filler in the resole, and thereafter adding the hardener. Uniform distribution of both the filler and the hardener throughout the composition is essential for the production of uniformly textured foam products and therefore thorough mixing is required.

If it is desired that the composition is at elevated temperature prior to commencement of the exothermic reaction, this can be achieved by heating the resole or first mixing the resole and the solid and then heating the mixture. Preferably the solid is added to the resole just before the addition of the hardener. Alternatively, the mixture of resole, solid and hardener may be prepared and the whole mixture then heated, for example by short wave irradiation, preferably after it has been charged to a mould. A conventional radiant heat oven may also be used, if desired, but it is difficult to achieve uniform heating of the mixture by this means.

Laminated Filter Structures

The laminated filter structures of the invention comprise the foam filters of the invention and at least one layer of additional material bonded to at least one surface of the foam filter. The laminated filter structures can be standalone self-supported filter structures, or they can be included as a component of a larger structure such as a wall, ceiling, floor or door of a room. In other embodiments, the laminated filter structure structures can be included as a component of furniture present in a room, such as tables, chairs, beds or sofas, or included in other structural or decorative features of a building such as in pillars. In some embodiments, the laminated filter structures can comprise straight external surfaces, for example, for inclusion in a wall of a room. In other embodiments, the laminated filter structures can have curved outer surfaces such as for inclusion in a wall with a curved surface. In yet further embodiments, the filter structures can be curved so as to extend around corners such as the borders of two walls or a wall and a ceiling. In these embodiments, the filter structures are a component of both walls, or a wall and a ceiling. The filter structures may also curve along their entire length at a constant or near constant gradient, for example when included in a pillar. The filter structures, can in essence, have any suitable three-dimensional shape, provided that said shape does not impact their filtering function. Since the filter structures can be incorporated in larger structural components as discussed above, or stand-alone self-supported structures, the filter structures can have a wide variety of three-dimensional shapes and configurations. The term laminated filter structure as used herein is thus not intended to be limited to any particular sub-set of three-dimensional shapes. The filter structures may also have any suitable dimensions for successful inclusion in any of the structures discussed above, or for fabrication as a stand-alone self-supported structure.

The term "laminated" as used herein in the context of a laminated filter structure or laminated filter panel is used to refer to a structure that comprises separate layers of material. Accordingly, the filter structures of the invention comprise the foam filters of the invention and at least one additional layer of material in contact with the foam filter. The at least one layer of additional material may simply be in contact with the foam filter, and it is not required that said additional material is bonded to the foam filter. However, in preferable embodiments, the at least one layer of additional material is bonded to a surface of the foam filter. The term "bonded" as used herein in the context of a laminate filter structure and the layer of additional material present therein is used to refer to the layer of additional material being attached to a surface of the foam filter. The term "bonded" is not limited to any particular chemical bond or any particular form of attachment. For example, the layer of additional material can be bonded to the foam filter by an adhesive. However, in preferable embodiments, the bonding is achieved by pressing the layer of additional material to the foam filter, as is described below in further detail.

The term panel as used herein is typically used to refer to filter structures that have a generally two-dimensional shape. For example, a rectangular shaped panel would typically have a larger length and width than thickness. As discussed above in the context of the term filter structures, filter panels may also have any of the curved surfaces discussed above, or curve around corners as discussed above.

The at least one layer of additional material preferably comprises at least one skin of sheet-form material, such as thermoset material such as SMC (sheet moulding compound), BMC (bulk moulding compound), or AMC (such as described above). However, it is not essential that the at least one layer of additional material is a thermoset material. For example, the at least one layer of additional material could be made from conventional building materials such as gypsum, or other materials suitable for inclusion in walls, ceilings, or floors etc.

In some embodiments, the at least one layer of additional material forms a portion of an outer surface of the structure, wherein the at least one layer of additional material does not cover the entirety of the at least one surface of the foam filter such that a portion of the at least one surface of the foam filter is exposed as a portion of the outer surface of the structure. In these embodiments, it is preferred that the at least one layer of additional material forms the very outer surface of a wall or ceiling etc. and is exposed to the room, however, it is not essential. For example, the laminated filter structure of the invention could comprise the foam filter with the at least one layer of additional material in contact with the foam filter. Adjacent to the at least one layer of additional material that forms part of the outer surface of the filter structure of the invention could be a further layer of material between the filter structure of the invention and the interior space of a room. However, in these embodiments, it is of course desired that the filter structure of the invention comprising the foam filter and at least one layer of additional material is in fluid communication with the interior open space of the room so that air from the interior space of the room can be drawn through the filter structure. However, as discussed above, preferably, the at least one layer of additional material forms the very outer surface of a wall or ceiling etc. and is exposed to the interior of the room.

In other embodiments, the at least one layer of additional material comprises at least one aperture extending therethrough between the at least one surface of the foam filter and an outer surface of the at least one layer of additional material, wherein the outer surface of the at least one layer of additional material forms the outer surface of the structure. Similarly to as described above, in these embodiments, preferably, the outer surface of the at least one layer of additional material that forms the outer surface of the laminated filter structures also forms the very outer surface of the wall, ceiling, floor, etc. that the laminated filter structure is a component of, so that the at least one layer of additional material is exposed directly to air, such as air present in the interior of a room. However, in alternative embodiments, the at least one layer of additional material that forms the outer surface of the laminated filter structures could of course be adjacent to a further layer of material that sits between the filter structure of the invention and air, e.g. in the interior space of a room. However, in these embodiments, it is of course desired that the filter structure of the invention comprising the foam filter and at least one layer of additional material is in fluid communication with the air such as in an interior open space of the room so that air can be drawn through the filter structure. Such fluid communication could be achieved, by for example the formation of apertures in the layer of further material.

In some embodiments, a section or all of the at least one additional material of the filter structures of the invention is removable from the filter structures of the invention. This feature can be very useful if it is desired for example, to replace a component of the filter structures of the invention, such as the at least one layer of additional material or the foam filter. In some embodiments, it may be desirable to replace the foam filter after a certain time period of use. Alternatively, it may be desirable to clean the foam filter after a certain time period of use. Such cleaning may require the removal of all or a segment of the at least one layer of additional material such that the foam filter may be effectively accessed.

Preferably, the at least one layer of additional material comprises a plurality of apertures therein, wherein the plurality of apertures extend through the at least one layer of additional material between the at least one surface of the foam filter and an outer surface of the at least one layer of additional material. The apertures can be introduced to the at least one layer of additional material using techniques that are known in the art. Preferably, the plurality of apertures comprise a plurality of perforations, such as micro-perforations or macroperforations. In preferred embodiments, the perforations are as described above. Such a perforation size has been found optimum for the drawing of air through the at least one layer of additional material so that the air is drawn into the phenolic foam filter. In other embodiments, the at least one aperture can be larger apertures present in the at least one layer of additional material instead of a plurality of perforations.

It is preferred that the at least one layer of additional material is non-porous or at least comprises a non-porous region. This is particularly preferred when the at least one layer of additional is in directly exposed to air such as air at the interior of the room, for example where the layer of additional material forms the outermost surface of a wall or ceiling. Preferably, the at least one skin of sheet-form material, which preferably comprises a thermoset material, optionally further comprising carbon fibres, glass fibres, aramid fibres, metallic fibres or any combination thereof. Such materials are known in the art and include SMC (sheet moulding compound), BMC (bulk moulding compound), or AMC such as described above.

The laminated filter structures of the invention can be fabricated using suitable methods in the art. For example, the foam filters and at least one layer of additional material can be fabricated separately before being bonded together, for example by an adhesive.

Where the at least one layer of additional material comprises at least one skin of sheet-form material, the sheet-form material can be cured first before being attached to the foam filter. However, in preferable embodiments, the at least one skin of sheet-form material is fabricated by a process involving placing an uncured composition in to contact with the foam filter, and then curing the uncured composition so as to form the cured sheet-form material bonded to the foam filter. In this regard, the foam filter acts as a substrate for the curing of the sheet-form material. Such a pressing process is disclosed in WO2018/220383 and WO2009/044169. Accordingly, in a preferable embodiment, the laminated filter structure is obtained or obtainable by a curing process comprising the steps of: providing a sheet-form curable material; providing the foam filter; and pressing the sheet-form material to the foam material; and optionally wherein gas and/or vapour can be displaced from the pressing region through the foam filter.

In some embodiments, the foam filter comprises crushable material, and the foam filter is crushed during the pressing step. Preferably, the step of applying pressure bonds the sheet-form material to the foam filter. Preferably, the method further comprises applying heat to the sheet-form material. Preferably, the sheet-form material is heated to a temperature greater than about 100° C., preferably greater than 120° C. Preferably, a portion of the sheet-form material flows into the surface of the foam filter during the pressing step. Preferably, method includes the step of applying the layer of sheet-form material to a mould, the method further including the step of pressing the substrate to the sheet-form material on the mould. The method may further include a step of providing a veil between the sheet-form moulding material and a surface of the mould. Typically, wherein the viscosity of the sheet-form material is reduced during the pressing step. Typically, the sheet-form material is applied as a substantially single thickness. Preferably, the pressure applied is less than 10 $kg/cm^2$, preferably less than about 6 $kg/cm^2$, and even as low as 4.5 $kg/cm^2$. Typically, the sheet-form material is applied to a mould surface comprising aluminium or aluminium alloy.

In preferable embodiments, where the at least one layer of additional material comprises at least one skin of sheet-form material, the material of the at least one skin of sheet-form material is mechanically keyed with the at least one surface of the foam filter, preferably wherein the sheet-form material extends into the cells of the open-celled phenolic foam. Such features are readily achievable using the methods described above.

As discussed above, the phenolic foam filter may comprise one or more grooves, channels, hollows or indentations so as to improve the flow of air through the laminated filter structure. Such features may be desired so as to increase the ease with which air is drawn through the filter, reducing the pressure requirements needed to displace the air.

The at least one layer of additional material may also comprise one or more grooves, channels, hollows or indentations within its outer surface, such that an outer surface of the structure comprises one or more grooves, channels or indentations therein. This is particularly preferred when the at least one layer of additional material forms the surface of a wall or floor etc. that is in direct contact with air in the interior of a room. Preferably, the one or more one or more grooves, channels, hollows or indentations comprise the one or more apertures or perforations present therein, preferably wherein the perforations or apertures are at the deepest part of the apertures or perforations. The one or more one or more grooves, channels, hollows or indentations present in the outer surface of the at least one additional material are preferably configured so as to direct saliva particles present in air towards the at least one aperture. This can be achieved in a variety of ways. For example, the grooves or channels can be of a shape and geometry that promote air flow towards the apertures or perforations so that saliva particles suspended in the air are directed towards the apertures, such that they can pass through the apertures and into the foam filter.

In some embodiments, the outer layer of the at least one layer of additional material comprises an anti-microbial coating on its outer surface. This is particularly preferred when the outer surface of the at least one layer of additional material is in direct contact with the air present in for example a room. Any suitable antimicrobial agent can be used as the coating, such as those discussed above. Methods of attaching the antimicrobial coating to the material are those known in the art.

Systems and Methods for Sanitising Air

There is also provided a system for the sanitisation of air, wherein the system comprises:

(i) a chamber comprising one or more foam filters according to the first aspect of the invention, or laminated filter structures according to the second aspect of the invention within the chamber, wherein the one or more foam filters or one or more laminated filter structures are in fluid communication with an interior of the chamber;
(ii) one or more conduits configured for drawing air from an interior of the chamber, through the one or more foam filters or one or more laminated filter structures and into the one or more conduits; and optionally
(iii) means for actively replacing the air drawn from the interior of the chamber with additional air.

Preferably, the chamber is a room, for example a room in a building. However, the chamber can also be for example the interior of a train, bus, boat or aeroplane etc. The means for actively replacing the air drawn from the chamber and the one or more foam filters or laminated structures can be the only means of drawing air into or out of the chamber. However, this is not essential and in other embodiments, the chamber can have an alternative means of replacing or withdrawing air from inside it. For example, the chamber can be substantially unsealed such as by a window or other aperture being present, or a wall or roof being absent. In other embodiments, the chamber can be substantially sealed other than for air being replaced in to withdrawn from the chamber with the means for actively replacing the air drawn from the chamber and the one or more foam filters or laminated structures. In preferable embodiments, the chamber comprises a floor, ceiling, several walls, a floor, and a door, although it is not essential that the chamber comprises all of these components. The chamber can be small such as a compact toilet, or the chamber may be far larger such as a sports hall or conference centre etc. It thus envisaged that the system of the invention is implementable in a wide variety of different chambers such as a wide variety of rooms of different sizes and shape.

As discussed above, the system contains one or more foam filters or laminated filter structures of the invention within the chamber. These are preferably built into the walls, ceiling or floor of the chamber, or furniture present within the chamber. In alternative embodiments, particularly where the system comprises a foam filter of the invention but not a laminated filter structure of the invention, the foam filter may be a self-supported stand-alone unit within the chamber.

The one or more conduits configured for drawing air from an interior of the chamber, through the one or more foam filters or one or more laminated filter structures and into the one or more conduits may comprise a pipe in fluid communication with the foam filters. The pipes or conduits may be connected to a means of lowering pressure within the conduit such as a vacuum pump, or other means known to the skilled person. When the means of lowering pressure is activated, the air pressure within the conduit is lowered. This causes a mild suction force extending through the foam filter and one or more layers of additional material if present extending into the interior of the chamber, which is made possible by the open-celled structure of the foam. Air is then drawn through the one or more layers of additional material if present and into and through the foam filter. Within the foam filter, the air contacts the antimicrobial agent present therein which kills or at least inhibits the action of microbes present therein. The microbes can be present in tiny saliva particles suspended in the air in the form of an aerosol. The saliva particles are drawn into the foam filter and through the pore structure of the material exposing the microbes therein to the antimicrobial agent. The air is then drawn from the filter into the conduit by the pressure gradient. The saliva particles present in the air may be drawn through the filter into the conduit. Alternatively, the saliva particles may remain within the pore structure of the foam filter. If this occurs, the foam filter may need to be cleaned occasionally as discussed above so as to remove the remnants of saliva particles present in the pore structure. It is not essential that the microbes are present in suspended saliva particles, and microbes may be suspended in the air without being present in saliva. The system of the invention may also be used to kill or inhibit such microbes. Suitable means for inducing vacuum such as pumps are known in the art. Appropriate pressures to employ to draw air through the filter and cause it to circulate within the chamber will be apparent to the skilled person. Such pressures will be dependent upon the nature of the chamber itself such as its size and shape, and also dependent upon the nature, size, dimensions and configuration of the filter structures or foam filters themselves. Whilst suitable pressures may vary, such pressures will be readily determinable with techniques known in the art. Once the air has been drawn into the conduit, the air may be disposed of into the atmosphere, or reintroduced back into the chamber. In this respect, the sanitisation system acts a sanitisation and recycling system. In this embodiment, the air may optionally be further processed or treated before reintroduction to the chamber.

An advantage of the system of the invention is that the foam filter or filter structures of the invention can be present over a large area of the chamber (such as over a large area of the walls or floor), because they are light, and can be effectively integrated into existing structures of the chamber. As such, air can be drawn out of the chamber over a large surface area (in contrast to for example large systems where air is drawn out of a single aperture connected to a conduit). In systems of the invention, the one or more conduits configured to draw air from the interior of the chamber can be placed parallel to a filter structure or foam filter of the invention such that the foam filter is in contact with the conduit along a whole or significant portion of its length. As such, air can be drawn from over a large surface area and introduced to a single conduit. Such a system has been found to be more efficient than a system for example where air is drawn out of a single aperture connected to a conduit. Accordingly, in a preferable embodiment, the one or more conduits configured for drawing air from an interior of the chamber, through the one or more foam filters or one or more laminated filter structures and into the one or more conduits is positioned such that air drawn from the filter can enter the conduit at several points along its length, and more preferably over a majority of its length, instead of only at the apertures at either end of the conduit.

The means for actively replacing the air drawn from the interior of the chamber with additional air is preferably configured so as to replace air drawn out of the chamber by the foam filters or filter structures. For example, the means for actively replacing air can be responsive to a change in air pressure in the chamber and configured so as to maintain the air pressure in the chamber at a constant or near constant pressure, such as atmospheric pressure by introducing air into the chamber as it is drawn out. Preferably, the air that is introduced to the chamber is cleaned or sanitised air, for example recycled air that has been cleaned and sanitised using a system of the invention and optionally further processed for reintroduction to the chamber.

The means for actively replacing air drawn from the interior chamber; the foam filters or filter structures; and the conduits configured to draw air from the chamber and through the filters or filter structures of the invention may together form a ventilation system. Preferably, the ventilation system or air sanitisation system of the invention are configured so as to minimise or eliminate horizontal air currents within the chamber. This may be done in a majority of ways. Preferably, although not essentially, this is achieved by configuring the means for actively replacing air drawn from the interior of the chamber so as to be in fluid communication with an aperture present in a ceiling of the chamber, and the one or more foam filters or one or more filter structures of the invention are a component of a structure (or a stand-alone structure themselves) at a lower position within the chamber, such as a component of the floor of the chamber, a lower portion of the walls of the chamber, furniture on the floor of the chamber, or as a stand-alone structure on the floor of the chamber. Such positioning causes air to be drawn from a lower portion of the chamber into the filters. Air is then introduced to the chamber at an upper position and travels vertically down towards the air filters as the air at the lower portion of the chamber is drawn through the filters. Such a configuration promotes vertical air currents in the chamber from the ceiling towards a lower part of the chamber, and minimises the induction of horizontal air currents. Similar configurations for achieving vertical air currents and minimising induction of horizontal air currents may also be used. Avoiding horizontal air currents and promoting vertical air currents is desirable since a portion of air that may contain saliva particles containing microbes is directed downwards and straight into the foam filters for sanitization instead of being directed across the chamber in a horizontal direction. Such horizontal air currents may cause the saliva particles to travel into contact with people in different section of the room, thus potentially infecting them with the microbes present in the saliva. Accordingly, such horizontal air currents are preferably avoided.

Such systems as described herein have been found capable of replacing all of the air in a chamber, constructed from the filter panels described herein, such as for example a 4 m×4 m×3 m (width×length×height) room, in a period of time from 40 minutes to 4 hours, depending on the available open-cell quantity and pore diameter used. This therefore provides a cost-efficient and rapid method of improving air quality and safety in a confined space, such as found in buildings (offices, hotels); transport (boats) and medical facilities.

The systems of the present inventions may additionally comprise sterilisation modules through which the drawn air may be passed. By way of example, the air may be passed through a suitable material such as a liquid to further sterilise it. It will be appreciated that such a step may be performed prior to, or after removal from, a chamber. Such an embodiment may be particularly advantageous where highly sterilised air is required or it is intended to recycle the air drawn out from the chamber.

The systems of the present inventions may also comprise means for controlling the quality of the air prior to entry into a chamber. By way of example, the system may comprise means for controlling the oxygen content of the air entering a chamber.

In some embodiments, the means for actively replacing air within the interior of the chamber can be a foam filter or filter structure of the invention. In such embodiments, the system essentially comprises foam filters or filter structures of the invention with the air flow direction essentially reversed relative to the foam filters and filter structures that are being used to draw air from the chamber. This can be done simply by adapting the conduit in contact with the foam filters to direct air into the interior of the chamber through foam filters. This can be done by using a pump to apply high pressure to the interior of the conduit forcing air out into and through the filters and into the chamber interior, or this can be done without the application of any high pressure, and the air can be drawn from the conduit simply by virtue of the air pressure within the chamber being lowered in response to air being drawn out of it. This particular embodiment is useful since air is sanitised both on entering and exiting the chamber.

When air is drawn into the foam filters or filter structures of the invention, by low pressure induced within the conduit in contact with the foam filters, the filter structures are preferably configured such that air travels through the perforations of the at least one layer of additional material and into the foam filters, or directly into the foam filters via the outer surface of the filter structures that are not covered by the at least one layer of additional material. As discussed above, the at least one layer of additional material that forms the outer surface of the filter structure is preferably in direct contact with the air in the interior of the room, for example, as the outer surface of a wall or floor of the chamber. However, although not preferred, in some embodiments, the filter structure comprising the foam filter and at least one layer of additional material are separated from the interior of the chamber by a further material layer. Air from the interior of the chamber can be in fluid communication with the filter structures by a variety of means such as further apertures being present in the outermost wall surface facing the chamber interior, or other configurations.

The system of the present invention is also envisaged in being useful in the event of a fire. Where the chamber comprises a room that is full of people, if a fire is detected in another part of the building, it may be desirable to completely seal and block off from air flow various other rooms present in the building (such as the chamber) so as to inhibit or eliminate the spreading of the fire. For example, it may be desirable to completely seal a chamber from air flow, so as to avoid the spread of fire to the chamber. However, if there are people present in the chamber, such airtight sealing cannot be performed for too long, because the people within the chamber still need oxygen for breathing. The system of the invention is particular useful in this scenario because it enables a chamber to be sealed and rendered completely airtight, other than air being able to enter or leave the chamber via the components of the system of the invention. The chamber can thus be sealed (other than at the components of the system of the invention) so as to retard the spread of fire within the building, whilst still providing fresh air to the people within the chamber, and evacuating exhaled air. Similarly, in the event of a fire, the system of the invention can be used to evacuate smoke that may be present within the chamber, or even reduce the amount of air in a chamber so as to retard (and potentially stop) the spread of fire.

Embodiments of the invention will now be described by way of example and with reference to FIG. 1.

EXAMPLE

FIG. 1 shows a sketch of a system of the invention implemented into a room (1). The room is a 4 m×4 m×3 m room (width×length×height). The direction of air flow is shown by the arrows (2) within the room. Air is drawn from the interior of the room through micro-perforations (3) in the wall (4) and into foam filters (5) of the invention that are present within the wall (4). The air passes through the foam filters (5) and into the conduits (6) shown in the floor and walls (4) of the room (1) where it is drawn away. The air can be recycled and reintroduced to the room (1), or released into the atmosphere. The air can be drawn into the conduits (4) by vacuum pumps (not shown) or similar apparatus for inducing a low pressure within the conduits. Air can be reintroduced into the room so as to maintain a constant pressure in the room (1) by means (7) for reintroducing air (not shown). In the system shown, the means (7) for reintroducing air is another conduit (8) which is positioned such that its aperture is within the roof of the room (1). The vertical air current formed by air entering the room (1) from the means (7) for reintroducing air is shown in the FIGURE by arrow (9). The exemplified foam filter is formed as part of a 1 m×1 m×50 mm panel and comprises a skin of sheet-form material on the surface facing the interior of the room. The skin of sheet-form material comprises the perforations therein. The foam filter has an internal surface area of from 50 $m^2$ to 300 $m^2$, and the system is configured such that the air drawn from the room travels through this surface area of foam between the perforations and conduits. The foam filter comprises 25% by weight of a finely divided particulate copper antimicrobial agent, which is dispersed substantially uniformly in the foam matrix. It was found the air within the room can all be withdrawn via the filter and replaced with additional air within a time period of around 4 hours using, for example, a small pump producing about 1 hp.

The invention claimed is:

1. A foam filter for filtering air comprising an open-celled phenolic foam, the open-celled phenolic foam having an accessible pore volume of from 0.5 $m^3$ to 0.96 $m^3$ per $m^3$ of foam, the open-celled phenolic foam comprising cells having an average cell size of from 0.5 mm to 7 mm; and the phenolic open-celled foam further comprising an antimicrobial agent, wherein the open-celled phenolic foam has a density of from 80 kg/$m^3$ to 800 kg/$m^3$.

2. A foam filter according to claim 1, wherein the antimicrobial agent comprises a finely divided particulate solid having antimicrobial properties, or wherein the antimicrobial agent comprises a fiber-containing material with antimicrobial properties.

3. A foam filter according to claim 1, wherein the open-celled phenolic foam comprises cells having an average cell size of from 3 mm to 6 mm.

4. A foam filter according to claim 1, wherein the open-celled phenolic foam is rigid.

5. A foam filter according to claim 1, wherein the antimicrobial agent is present in the open-celled phenolic foam in an amount of from 5% by weight to 50% by weight of the foam material.

6. A foam filter according to claim 1, wherein the antimicrobial agent comprises a finely divided particulate solid having antimicrobial properties with a particle size of from 0.2 to 800 μm.

7. A foam filter according to claim 1, wherein the antimicrobial agent is an antibacterial agent, an antiviral agent, or a combination thereof.

8. A foam filter according to claim 1, wherein the antimicrobial agent comprises metal particles or fibers, wherein the metal comprises copper, titanium, silver, aluminium, cobalt, zinc, zirconium, molybdenum, tin or lead.

9. A foam filter according to claim 1, wherein at least a portion of the antimicrobial agent is present at a surface of the open-celled phenolic foam.

10. A laminated filter structure comprising a foam filter according to claim 1, and at least one layer of additional material in contact with at least one surface of the foam filter, wherein the at least one layer of additional material is bonded to the at least one surface of the foam filter, wherein:

(i) the at least one layer of additional material forms a portion of an outer surface of the structure, wherein the at least one layer of additional material does not cover the entirety of the at least one surface of the foam filter such that a portion of the at least one surface of the foam filter is exposed as a portion of the outer surface of the structure; or (ii) the at least one layer of additional material comprises at least one aperture extending therethrough between the at least one surface of the foam filter and an outer surface of the at least one layer of additional material, wherein the outer surface of the at least one layer of additional material forms the outer surface of the structure.

11. A laminated filter structure according to claim 10, wherein the at least one layer of additional material comprises a plurality of apertures therein, wherein the plurality of apertures extend through the at least one layer of additional material between the at least one surface of the foam filter and an outer surface of the at least one layer of additional material.

12. A laminated filter structure according to claim 10, wherein a further layer of additional material is bonded to an opposing surface of the foam filter, such that the foam filter is sandwiched between the layers of additional material.

13. A laminated filter structure according to claim 12, wherein the at least one skin of sheet-form material comprises a thermoset material.

14. A laminated filter structure according to claim 10, wherein the at least one layer of additional material is mechanically keyed with the at least one surface of the foam filter, and wherein the additional material extends into the cells of the open-celled phenolic foam.

15. A laminated filter structure according to claim 10, wherein the laminated filter structure is obtained or obtainable by a curing process comprising the steps of: providing at least one layer of additional material; providing a foam filter; and pressing the at least one layer of additional material to the foam filter; and wherein gas and/or vapour can be displaced from the pressing region through the foam filter.

16. A laminated filter structure according to claim 10, wherein the foam filter comprises one or more grooves, channels, hollows or indentations so as to improve the flow of air through the laminated filter structure; and/or wherein the at least one layer of additional material comprises one or more grooves, channels, hollows or indentations within its outer surface, such that an outer surface of the structure comprises one or more grooves, channels or indentations therein.

17. A laminated filter panel according to claim 10, wherein the at least one layer of additional material comprises an anti-microbial coating on its outer surface, such that the antimicrobial coating is disposed upon a portion of the outer surface of the filter structure.

18. A system for the sanitization of air, wherein the system comprises:

(i) a chamber comprising one or more foam filters according to claim 1, or laminated filter structures according to claim 10 within a chamber, wherein the one or more foam filters or one or more laminated filter structures are in fluid communication with an interior of the chamber;

(ii) one or more conduits configured for drawing air from an interior of the chamber, through the one or more foam filters or one or more laminated filter structures and into the one or more conduits.

19. A system according to claim 18, wherein the one or more foam filters or one or more filter structures are a component of at least one member of a group comprising: one or more walls of the chamber; one or more doors of the chamber, the floor or ceiling of the chamber, furniture within the chamber, and structural features.

20. A foam filter according to claim 1, wherein at least 50% of the cells present in the open-celled phenolic foam have a cell size of from 3 mm to 6 mm.

* * * * *